US009359240B2

(12) United States Patent
Bouchet et al.

(10) Patent No.: US 9,359,240 B2
(45) Date of Patent: Jun. 7, 2016

(54) METHOD FOR DESULPHURATION OF THE DIGESTATE AND THE BIOGAS OF A DIGESTER, AND BIOGAS PRODUCTION FACILITY IMPLEMENTING SAID METHOD

(75) Inventors: Caroline Bouchet, Maule (FR); Roger Nicol, Issy-les-Moulineaux (FR); Claude Prevot, Velizy (FR)

(73) Assignee: DEGREMONT (FR)

( * ) Notice: Subject to any disclaimer, the term of this patent is extended or adjusted under 35 U.S.C. 154(b) by 309 days.

(21) Appl. No.: 13/976,897

(22) PCT Filed: Dec. 23, 2011

(86) PCT No.: PCT/IB2011/055926
§ 371 (c)(1),
(2), (4) Date: Sep. 9, 2013

(87) PCT Pub. No.: WO2012/090139
PCT Pub. Date: Jul. 5, 2012

(65) Prior Publication Data
US 2013/0341269 A1    Dec. 26, 2013

(30) Foreign Application Priority Data

Dec. 27, 2010 (FR) ..................................... 10 61265

(51) Int. Cl.
*C02F 11/04* (2006.01)
*C02F 3/28* (2006.01)
(Continued)

(52) U.S. Cl.
CPC . *C02F 11/04* (2013.01); *C02F 3/28* (2013.01); *C12M 21/04* (2013.01); *C12M 29/18* (2013.01);
(Continued)

(58) Field of Classification Search
CPC ............ C02F 11/04; C02F 1/727; C02F 1/74; C02F 3/28; C02F 2101/101; C02F 2209/02; C02F 2209/22; C02F 2209/225; C02F 2209/26; C02F 2209/265; C02F 2209/40; C02F 2301/043; C02F 2301/106; C02F 2303/08; C12M 21/04; C12M 29/18; C12M 47/18; Y02E 50/343; Y02W 10/12
USPC .................. 210/603, 188, 252, 259, 194, 916
See application file for complete search history.

(56) References Cited

U.S. PATENT DOCUMENTS 5,500,123 A * 3/1996 Srivastava ..................... 210/603
7,374,682 B2 * 5/2008 Kamachi ............... C02F 3/2846
210/603
(Continued)

FOREIGN PATENT DOCUMENTS

EP    1970353        9/2008
FR    2461684 A1 *  2/1981
(Continued)

OTHER PUBLICATIONS

Machine-generated English translation of FR 2484990, generated on Jul. 13, 2015.*

*Primary Examiner* — Fred Prince
(74) *Attorney, Agent, or Firm* — The Belles Group, P.C.

(57) ABSTRACT

The invention relates to a method for desulphuration of the digestate and biogas in a digester (1) of urban and/or agricultural and/or industrial effluent, by biochemical and/or thermochemical processes, the digester consisting of an enclosure (2) which is closed at the top, in which anaerobic digestion of a mass of products to be treated making up the digestate (4) takes place, the digester comprising at least one loop (10) for external recirculation of the digestate; an oxidant is injected at least at one point (13, 14) of the loop (10), the injection conditions being as follows: the speed of circulation of the digestate in the loop (10) must be high enough to prevent the deposition of sulphur on the walls of the pipes; the contact time between the injected oxidant and the recirculated digestate recirculated from the injection point (13, 14) of the oxidant until the reinjection point (11b) of the digestate must be long enough for all the oxidant to be dissolved in the liquid phase of the digestate; the amount of oxygen in the oxidant injected into the recirculation loop must be low enough to avoid the presence of oxygen in the biogas, but high enough to eliminate the hydrogen sulphide from the biogas.

13 Claims, 4 Drawing Sheets

(51) Int. Cl.
  *C02F 1/74*   (2006.01)
  *C12M 1/107*  (2006.01)
  *C12M 1/00*   (2006.01)
  *C02F 1/72*       (2006.01)
  *C02F 101/10*     (2006.01)

(52) U.S. Cl.
  CPC ............... *C12M 47/18* (2013.01); *C02F 1/727* (2013.01); *C02F 1/74* (2013.01); *C02F 2101/101* (2013.01); *C02F 2209/02* (2013.01); *C02F 2209/22* (2013.01); *C02F 2209/225* (2013.01); *C02F 2209/26* (2013.01); *C02F 2209/265* (2013.01); *C02F 2209/40* (2013.01); *C02F 2301/043* (2013.01); *C02F 2301/106* (2013.01); *C02F 2303/08* (2013.01); *Y02E 50/343* (2013.01); *Y02W 10/12* (2015.05)

(56) References Cited

U.S. PATENT DOCUMENTS

2005/0029189 A1   2/2005  Langhans
2005/0139546 A1*  6/2005  Burke ...................... C02F 1/20
                                                       210/603

FOREIGN PATENT DOCUMENTS

FR      2484990 A2 *  12/1981
JP      2005329377    12/2005

* cited by examiner

METHOD FOR DESULPHURATION OF THE DIGESTATE AND THE BIOGAS OF A DIGESTER, AND BIOGAS PRODUCTION FACILITY IMPLEMENTING SAID METHOD

PRIORITY

Priority is claimed as a national stage application, under 35 U.S.C. §371, to PCT/IB2011/055926, filed Dec. 23, 2011, which claims priority to French application FR 1061265, filed Dec. 27, 2010. The disclosures of the aforementioned priority applications are incorporated herein by reference in their entirety.

The present invention relates to a method for desulfurating the digestate and the biogas, in other words removing sulfides from the digestate and hydrogen sulfide, or sulfide of hydrogen, from the biogas in a digester for urban and/or agricultural and/or industrial effluents, by a wet and/or dry route. By effluent is meant any liquid, pastelike or solid discharge (urban or industrial wastewaters, sludges obtained from urban or industrial effluent treatment, organic fraction of urban, industrial, or agricultural waste).

The digester consists of a chamber which is closed at the top, and anaerobic digestion of a mass of products to be treated takes place within said chamber. The upper part includes a gas space from which the biogas is withdrawn.

The field of the invention is that of anaerobic digestion, or methanization or fermentation, of urban and/or agricultural and/or industrial effluents (and/or residues and/or substrates) by a wet and/or dry route. This invention may be applied in plants for treating municipal and/or industrial wastewaters, plants for treating wastewaters, or for treating household refuse (fermentable fraction of household refuse and/or crude household refuse), and/or any type of biowastes (wastes from restaurants, canteens, unsold supermarket products, etc.), plants for treating agricultural residues (animal excrements, plant residues, etc.), plants for codigestion (anaerobic) or cofermentation or comethanization in which one or more substrates are mixed, and, ultimately, any plant producing biogas.

In the remainder of the text the single term "digestion" will sometimes be used, for simplification, in place of "anaerobic digestion" or "methanization" or "fermentation"; it is understood that the term "digestion" encompasses the terms methanization, digestion and/or fermentation. Similarly, the digestate corresponds to the overall volume or mass of the substrate digested or methanized or fermented.

At a time when environmental concerns are becoming ever greater and when alternatives are being sought to consumption of fossil energy, the anaerobic digestion/methanization/fermentation of effluents and/or residues has to be considered with great interest, since it allows the production of a biogas rich in methane that can be exploited for thermal, and/or electrical energy.

Given the composition of urban, agricultural or industrial effluents and/or residues, the biogas produced in the course of digestion contains hydrogen sulfide ($H_2S$) in amounts of between 0 and 20,000 ppm (parts per million), depending on the treatment applied prior to the anaerobic digestion/methanization/fermentation and on the substrates/effluents.

During the thermal and/or electrical exploitation of the biogas—by means of co- (or tri-)generation, boiler, flare, fuel cells, or indirectly by injection into the network, or conversion to biogas fuel—this hydrogen sulfide causes corrosion of the apparatus, and/or, by chemical conversion, produces toxic oxides of sulfur (SOx) whose discharges into the atmosphere are a subject of regulation.

It may also be noted that the efficiency of the digestion may be limited in the presence of a very substantial amount of hydrogen sulfide, since the latter is toxic toward some bacteria in the digestion.

Furthermore, the presence of sulfides dissolved in the digestate (in equilibrium with the amounts of hydrogen sulfide in the biogas) is manifested in a risk of subsequent degassing and in safety problems for those personnel who handle/treat/end-process the digestate.

Irrespective of the eventual destination of the biogas for exploitation, and of the outcome for the digestate, it proves vital to remove at least $H_2S$ from the biogas, and preferably to remove the sulfides from the digestate as well.

The sulfur cycle is complex. Under anaerobic conditions, the production of sulfides is inevitable. At the typical pH at which digesters (methanizers) operate, a major part of the sulfides are desorbed/stripped in the form of hydrogen sulfide in the biogas.

The removal of the sulfides from the digestate and/or of hydrogen sulfide from the biogas currently involves the following treatments being implemented:

upstream of the digester: for example, via injection of iron salts into the substrate(s) and/or effluents;

downstream of the digester: via post-treatment of the biogas, using chemical, physical, or biological reactions or a combination of these unit processes. This post-treatment comprises one or more reactors separate from the digester that treat the biogas after digestion of the effluents/substrates.

in the digester: via injection of iron salts or via microaeration.

These solutions are generally expensive in terms of investment costs and operating costs.

An alternative route uses biological oxidation of the sulfides, which is able selectively to produce native sulfur S°, a yellow solid which is or is not amorphous (depending on its state of purity and/or of crystallization). This is especially the case when the electron acceptor is oxygen and when this oxygen is present in small amounts (less than 0.1 mg/L). The sulfur-oxidizing bacteria are composed more particularly of Gram-negative bacteria of the types *Thiobacilius*, *Thiomicrospira* and *Thiosphaera*. Certain chemolithotrophic bacteria that use sulfides as electron donors are also capable of using the oxidized forms of nitrogen ($NO_2$ and $NO_3$) as electron acceptors. The implementation of this type of reaction, without compromising the anaerobic conditions favorable to methanogenesis, is precisely the aim of microoxidation.

Microoxidation in the digester is generally carried out by agricultural methanization, with small-capacity digesters corresponding, for example, to the effluents from a single agricultural enterprise. Microoxidation here is provided by injection of air into the upper gas space, also called top space, of the digester. The biochemical reaction produces sulfur S°, which forms localized stalactites beneath the dome of the digester. The main risks associated with this precipitation are as follows:

damage to the systems for agitating and recovering the digestate, in the event of harmful detachment of a mass of sulfur;

the risk of deposition throughout the biogas line, with damage to the associated equipment;

the excessive mass of sulfur, under the dome or under any other covering device, which may give rise to mechanical breakage.

These covered digesters are generally cleaned once a year in order to make up for this drawback. In the context of larger-scale plants, it is economically untenable to empty and clean a digester once a year.

The conventional recommendation is for emptying and cleaning-out every ten years.

Lastly, if the digester is not biogas-agitated, the preferential treatment of the biogas does not guarantee a proportional reduction in sulfides in the digestate and does not prevent a risk of subsequent degassing of hydrogen sulfide.

Digesters have been produced with specific biogas agitation in order to allow microaeration at the level of agitating pipes. The risk, on the one hand, is the blocking of the agitating pipes by precipitation of this sulfur S°, with a reduction in the efficiency of digestion as a result of poor homogenization; on the other hand, in this configuration, the risk is of very limited dissolution of oxygen in the digestate, with a residual risk of formation of deposits under the dome or the covering.

The disadvantages of the desulfuration processes described above come about in particular as a result of poor dissolution of air or the oxidant in the digestate, and of formation of native sulfur in highly localized zones, more particularly in the gas space of the digesters. A secondary effect of this accumulation of sulfur is to damage the hardware of the digester and/or the efficiency of digestion. These processes, moreover, do not allow complete desulfuration of the digestate, and the risks of subsequent entrainment (stripping) of hydrogen sulfide remain substantial.

A particular aim of the invention is to provide a method for desulfurization that no longer has these drawbacks and which is simple and economical to operate. It is desirable, furthermore, that the method can be implemented readily in an existing digester.

According to the invention, the method for desulfuration of the digestate and the biogas in a digester for urban and/or agricultural and/or industrial effluents, by wet and/or dry route, the digester consisting of a chamber which is closed at the top and in which anaerobic digestion of a mass of products to be treated takes place, forming the digestate, with a gas space above the digestate, from which the biogas is withdrawn, the digester comprising at least one external digestate recirculation loop, is characterized in that:
   the digestate withdrawal point is situated in the lower part of the digester, and the digestate is reinjected at a point at a liquid level higher than the withdrawal point,
   at least one point of the digestate recirculation loop, a gaseous or liquid oxidant is injected, the injection conditions being as follows:
   the circulation rate of the digestate in the loop is sufficient to prevent the deposition of sulfur on the walls of the lines in the recirculation loop,
   the contact time between the injected oxidant and the recirculated digestate, from the point of injection of the oxidant to the point of reintroduction of the digestate in the chamber, is sufficient for all of the oxidant to be dissolved in the liquid phase of the digestate,
   the amount of oxygen in the oxidant injected into the digestate is low enough to prevent the presence of oxygen in the biogas but high enough to remove hydrogen sulfide from the biogas, the desulfuration occurring in the biogas and in the digestate, and the sulfur produced remaining in the form of particles which are dispersed in the digestate and are removed together with it.

The amount of air or oxygen injected into the recirculation loop corresponds preferably to the amount that would produce an equivalent oxygen concentration of less than or equal to 0.65 X, where X is the saturation concentration of oxygen in pure water, estimated at the temperature and pressure of the recirculation loop.

This amount of air or oxygen injected into the recirculation loop corresponds advantageously to the amount that would produce an equivalent oxygen concentration of greater than or equal to 0.20 X, and preferably of between 0.60 X and 0.20 X.

The contact time between the injected oxidant and the digestate, from the point of injection to the point of reintroduction into the chamber, is at least 15 seconds.

The circulation rate of the digestate in the loop is at least 0.6 m/s, preferably at least 1 m/s (1 meter/second).

The oxidant injected is preferably gaseous and composed of air or oxygen.

The invention not only allows the removal of the hydrogen sulfide or sulfide of hydrogen from the biogas, but also the removal of the sulfides from the digestate or substrate.

The invention also relates to a plant for producing biogas, comprising a digester for urban and/or agricultural and/or industrial effluents, by wet and/or dry route, the digester consisting of a chamber which is closed at the top and in which anaerobic digestion of a mass of products to be treated takes place, forming a digestate, with a gas space above the digestate, from which the biogas is withdrawn, and at least one external digestate recirculation loop between a point of withdrawal from the chamber and a reintroduction point, said plant being characterized in that:
   the withdrawal point of the digestate is situated in the lower part of the digester, and the digestate is reinjected at a point at a liquid level higher than the withdrawal point,
   said plant comprises, at least one point in the recirculation loop, a device for injecting a gaseous or liquid oxidant,
   said plant includes a pump which circulates the digestate within the loop, the diameter of the piping of the loop and the capacity of the pump being selected such that the circulation rate of the digestate in the loop is sufficient to prevent deposition of sulfur on the walls of the lines in the recirculation loop,
   the length of piping in the loop between the injection point and the reintroduction point in the chamber is sufficient for all of the oxidant to pass into the liquid phase of the digestate before return to the chamber,
   and the amount of oxygen in the oxidant injected in the recirculation loop is low enough to prevent the presence of oxygen in the biogas and high enough to remove hydrogen sulfide from the biogas.

The recirculation loop may include a contact basin, especially with agitating means, to promote transfer of the oxidant into the recirculated phase.

The digestate withdrawal point for the recirculation loop is advantageously situated in the lower part of the digester, and the digestate reinjection point is situated at a liquid level higher than the withdrawal point, so as to limit the degassing of the oxidant.

The recirculation loop may comprise at least one heat exchanger for reheating the digestate and maintaining the digester at constant temperature. The heat exchanger may be a double-wall exchanger around a portion of the recirculation loop.

The invention, apart from the arrangements set out above, comprises a certain number of other arrangements which will be addressed more specifically hereinafter, using embodiment examples which are described with reference to the attached drawings, but which are in no way limitative. In these drawings.

Figure 7:
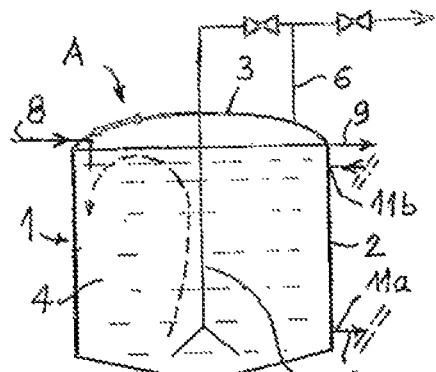
FIG. 7 is a vertical diagrammatic section through a plant according to the invention, with agitation of the digestate by an agitating pipe which reinjects biogas.
Figure 8:
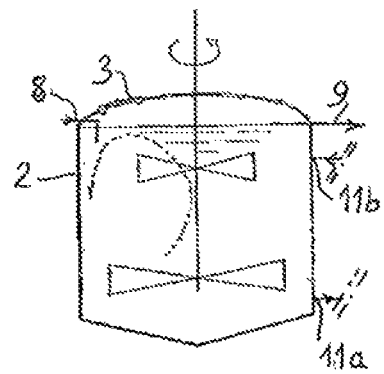
Figure 9:
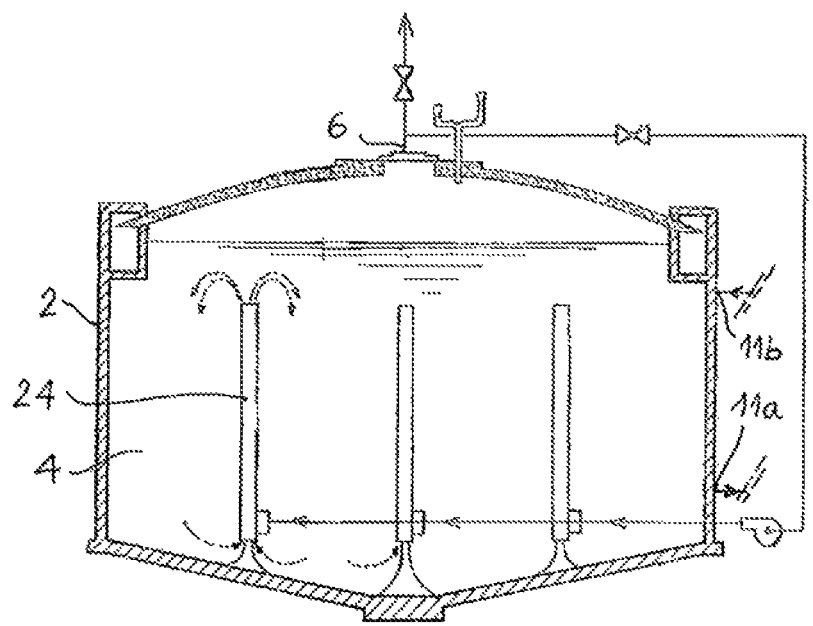

FIG. 8, similarly to FIG. 7, shows a plant with mechanical agitation of the digestate, and FIG. 9 is a diagrammatic section, similar to FIG. 7, of a variant with agitation of the digestate by gas bubble canisters.

Figure 1:
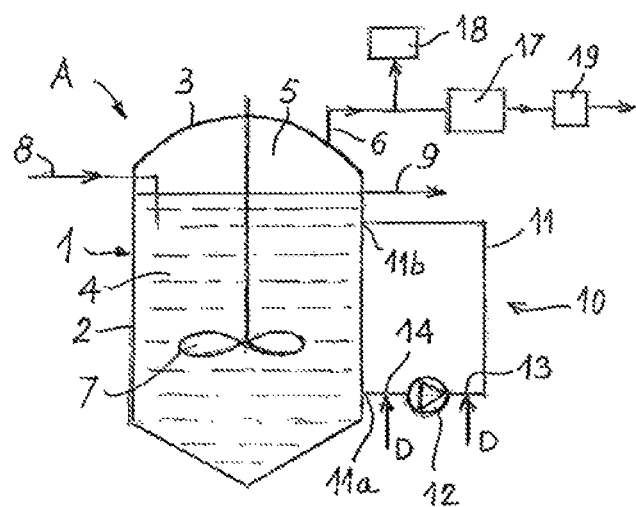
FIG. 1 is a diagrammatic vertical axial section through a plant with digester for implementing the desulfuration method according to the invention.

Referring to FIG. 1 of the drawings, it is possible to see a biogas production plant A comprising a wet-route digester 1 for urban and/or agricultural and/or industrial effluents. In a variant, a dry-route digester may be used. The digester 1 consists of a chamber 2 which is closed, in its top part, by a dome 3. Taking place in the chamber 2 is anaerobic digestion of a mass of products to be treated, forming a digestate 4, with a gas space 5, also called top space, above the digestate, from which the biogas is withdrawn via a line 6. Means of agitation for the digestate are provided, more particularly means 7 of mechanical agitation, formed by one or more screws carried by a rotary vertical shaft.

The products for treatment are introduced into the chamber 2 via a line 8, while the excess digestate is removed via an overflow line 9.

The plant includes at least one recirculation loop 10, formed by a line 11 connected at a withdrawal point 11*a* sited in the bottom part of the chamber 2, and a point 11*b* of reinjection into the chamber, sited in the top part.

A recirculating pump 12 is arranged on the line 11, to circulate the digestate from the withdrawal point 11*a* to the reinjection point 11*b*.

A device D for injecting a gaseous or liquid oxidant is provided at at least one point 13, 14 in the circulation loop. The injection point 13, according to the example of FIG. 1, is located downstream of the pump 12, whereas the injection point 14 is located upstream. A single injection point or more than two injection points may be provided.

The internal diameter of the line 11 in the loop 10, and the capacity of the pump 12, are selected such that the circulation rate of the digestate in the loop 10 is sufficient to prevent deposition of sulfur on the walls of the lines of the loop 10. This digestate recirculation rate is greater than 0.6 m/s (0.6 meter/second), and preferably greater than 0.8 m/s, advantageously greater than or equal to 1 m/s (1 meter/second).

The amount of air or oxygen injected by the oxidant injection device or devices D into the recirculation loop corresponds to the amount that would produce an equivalent oxygen concentration of less than or equal to 0.65 X, X being the oxygen saturation concentration in pure water, estimated at the temperature and pressure of the saturation loop.

This amount of air or oxygen injected into the recirculation loop corresponds preferably to the amount which would produce an equivalent oxygen concentration of greater than or equal to 0.20 X, and preferably of between 0.60 X and 0.20 X, in order to ensure a satisfactory sulfur precipitation yield.

The length of line in the loop 10 between the oxidant injection point 13, 14 and the point 11*b* of reinjection into the chamber 2 is selected to be sufficient for all of the oxidant to be dissolved in the liquid phase of the digestate before return into the chamber 2.

The invention thus relates to a method for desulfurating biogas by microoxidation that comprises an injection of air, oxygen, or any other oxidant into a digestate recirculation loop 10 external to the digester. The injection of oxidant, air or oxygen or any other oxidant in gaseous or liquid form, is advantageously performed by means of a device D which gives out fine or medium bubbles and is available commercially.

The length of the line 11 is determined such that it allows a sufficient contact time between the oxidant in gaseous or liquid form and the digestate, so as, where necessary, to dissolve and homogenize all of the oxidant within this recirculation loop. The diameter of the line 11 is determined as a function of a minimum sludge recirculation rate, in order to limit the localized deposits of native sulfur or solid sulfur in the S° form.

The invention thus provides for microoxidation of the substrates for digestion in an external recirculation loop 10, for the purpose of removing the sulfides from the digestate and from the biogas, and of preventing localized accumulations of sulfur. The sulfur formed is then in particulate form in the liquid or semiliquid phase, and is homogenized with the digestate/substrate by virtue of the agitating system 7 in the digester: the sulfur formed cannot accumulate and form agglomerates which are harmful to the digestion. This sulfur is subsequently removed with the digestate/substrate in batches or continuously or semicontinuously, depending on the operation of the digestion.

According to the example of FIG. 1, a single recirculation loop 10 is shown, but a plurality of external loops could be provided. The digestate recirculation rate for self-cleaning of the line 11 is at least 1 m/s, and is preferably greater than that value. The gaseous oxidant may be air or pure oxygen.

The digestate withdrawal point or points are sited in the lower part of the digester 1, and the digestate is reinjected at a point 11*b*, at a liquid level higher than the withdrawal point 11*a*. The pressure in the sludge is higher at the point 11*a*, near to the point at which oxidant is injected, and this is favorable for the dissolution of the oxidant. Moreover, any deposits of sulfur in the chamber 2 are drawn up by this withdrawal in the bottom part 11*a*.

Figures 2, 3:
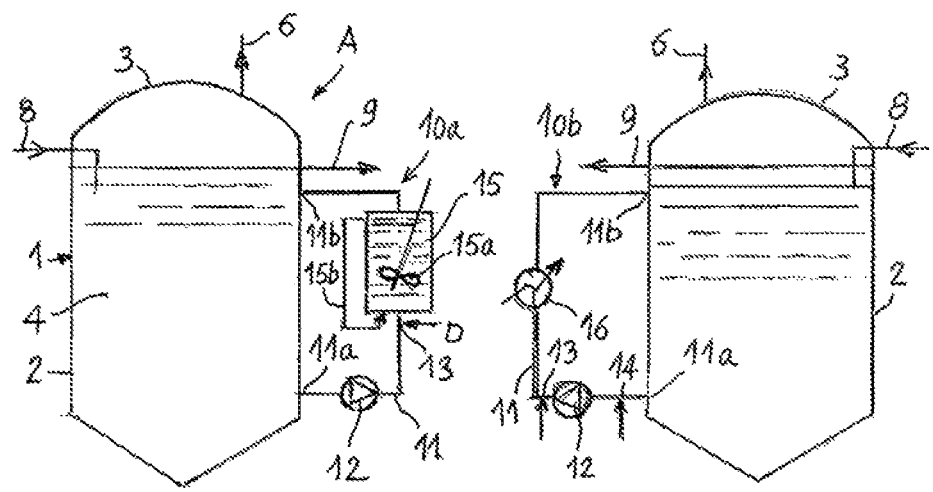
FIG. 2 is a vertical diagrammatic section through a variant of the plant according to the invention.
FIG. 3 is a vertical diagrammatic section through another variant embodiment of the plant according to the invention.

Those elements in the variants of FIGS. 2 and 3 that are identical or similar to elements already described in relation to FIG. 1 are denoted by the same references, and their description is not repeated or else they are described succinctly.

According to the embodiment example of FIG. 2, a contact basin 15, with agitating means 15*a*, is provided on the recirculation loop 10*a*. The basin 15 is formed by a capacity which is inserted into the loop and is fully filled with digestate, without a gas space. The injection point 13 may be sited just downstream of the inlet of the basin 15. A loop 15*b* for recirculating the concentrate fraction from the basin 15 may also be provided. The basin 15 could be provided without agitating means.

This basin 15 facilitates the transfer of the oxidant into the recirculated phase of the digestate. In the example of FIG. 2, the basin 15 is located downstream of the pump 12, but it could be installed upstream of said pump.

FIG. 3 illustrates a variant embodiment whereby the recirculation loop 10b includes a heat exchanger 16, which allows the digestate to be reheated by means of a heat transfer fluid, and allows the digester to be maintained at a constant temperature. The exchanger or exchangers 16 may be of double-case type around a portion of the line 11 in the recirculation loop 10b.

Exemplary Embodiments

The rules governing dissolution of oxygen in pure water are known (maximum transfer rate and maximum solubility) as a function of temperature and pressure. However, in more concentrated media such as sludges from industrial and/or municipal purification stations, liquid and/or semiliquid wastes, etc., these rules are not established: they are dependent on the concentration and on the type of product.

Tests were carried out on dissolution of oxygen/or air in different effluents, for the purpose of optimizing the desulfuration of the biogas and of the digestate on an industrial scale. Moreover, digestate desulfuration tests were carried out in order to characterize the rates above which a risk appears of deposit on the line.

Laboratory Tests

A 2.5 m³ reactor was used for the digestion. This reactor, of the same type as illustrated in FIG. 1, is held at temperature by a coil (not shown) which is placed in the digester, and hot water circulates within said coil. Said water does not come into contact with the sludge.

The supplying of the reactor via the line 8 is continuous and is obtained by means of a peristaltic pump (not shown) with an adjustable capacity. The emptying of the digester is performed by an overflow 9, which flows by gravity into a storage basin (not shown).

The feed sludge is withdrawn from a purification station at the end of thickening. According to the purposes of the experiment, this sludge may be a primary or mixed biological sludge.

The reactor 1 is agitated by a mechanical means 7 for ease of installation. The residence time of the sludge in the reactor 1 is variable. Two temperature conditions were employed:
   35° C. (mesophilic conditions) with a residence time of 20 days,
   and 55° C. (thermophilic conditions) and 12 days' residence time.

The recirculation line 11 was defined such that the recirculation rate is 2.5 m³/d; the recirculation rate is obtained by means of a peristaltic pump 12 referred to as a recirculating pump. The point of injection of the oxidant (air used in this example) is a point 13 situated downstream of the recirculating pump 12. The line downstream of this injection is made of transparent plastic. A number of diameters were used for lines 11, so as to vary the recirculation rate.

A slight overpressure in the digester 1 is provided by the positioning of a water hood 17 sited on the biogas withdrawal line 6. The biogas is analyzed continuously by an analyzer 18 connected to the line 6, with determination of the amounts of $CH_4$ (methane), $CO_2$ (carbon dioxide), $H_2S$ (hydrogen sulfide), and $O_2$ (oxygen).

An adsorption unit 19 may be provided on the line 6 downstream of the water hood 17, and the biogas leaving the unit 19 is directed toward a burner (not shown). The unit 17 is advantageously an active carbon adsorption unit.

In a first stage, the maximum amount of air that could be dissolved in the recirculated sludge was evaluated: the presence of oxygen in the biogas, signaled by the analyzer 18, was the indicator of incomplete dissolution of the oxidant. Following establishment of the maximum flow rate of air for injection, different-sized lines were used in order to establish the minimum rate to be applied in order to prevent or limit deposits of sulfur on the walls.

Amount of Oxygen that can be Dissolved

The tests were carried out with a line having an internal diameter of 6 mm, and with a recirculation rate of 1 m/s (1 meter/second). Different line lengths were used, corresponding to a different contacting time.

The concentration of oxygen in the sludge, following injection of oxidant, is expressed as a percentage of the theoretical oxygen saturation X in pure water under the pressure and temperature conditions of the test. A value of 0% corresponds to 0 mg/l of oxygen in the sludge. A value of 100% corresponds to the concentration X of oxygen in the sludge equal to that obtained at saturation in water, for a given temperature and a given pressure.

The results for a contact time of greater than or equal to 1.5 s are given in table I below and are summarized in the diagram of FIG. 4. The contact time corresponds to the time taken by the sludge to travel between the oxidant injection point and the point of reinjection into the digester.

TABLE I

For a contact time of greater then or equal to 15 s:

| Concentration of oxygen in the sludge, relative to the theoretical oxygen saturation X in water | Reactor temperature 35° C. | Reactor temperature 55° C. |
|---|---|---|
| 0% | Absence of oxygen in the biogas | Absence of oxygen in the biogas |
| 10% | Absence of oxygen in the biogas | Absence of oxygen in the biogas |
| 20% | Absence of oxygen in the biogas | Absence of oxygen in the biogas |
| 30% | Absence of oxygen in the biogas | Absence of oxygen in the biogas |
| 40% | Absence of oxygen in the biogas | Absence of oxygen in the biogas |
| 50% | Absence of oxygen in the biogas | Absence of oxygen in the biogas |
| 59% | Absence of oxygen in the biogas | Absence of oxygen in the biogas |
| 60% | Absence of oxygen in the biogas | Presence of oxygen in the biogas |
| 64% | Absence of oxygen in the biogas | Presence of oxygen in the biogas |
| 65% | Presence of oxygen in the biogas | Presence of oxygen in the biogas |
| 70% | Presence of oxygen in the biogas | Presence of oxygen in the biogas |
| 80% | Presence of oxygen in the biogas | Presence of oxygen in the biogas |
| 90% | Presence of oxygen in the biogas | Presence of oxygen in the biogas |
| 100% | Presence of oxygen in the biogas | Presence of oxygen in the biogas |

Figure 4:
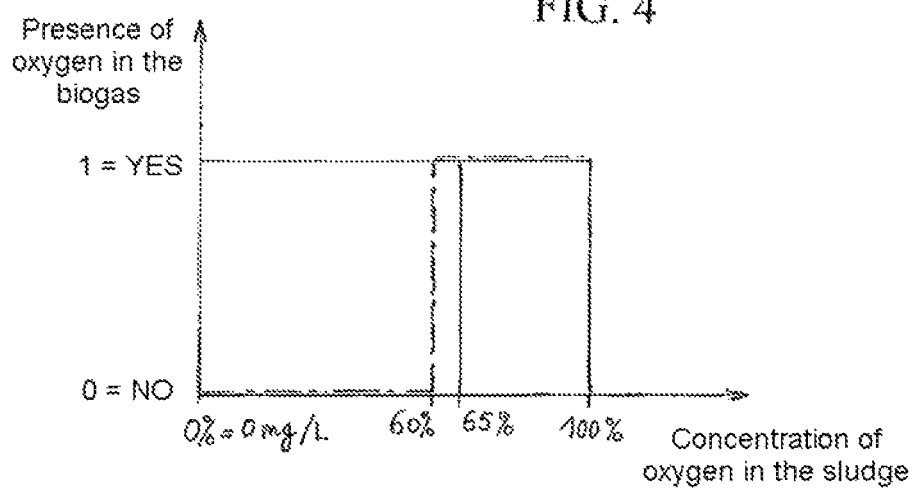
FIG. 4 is a diagram illustrating the presence of oxygen in the biogas, plotted on the ordinate, as a function of the concentration of oxygen in the recirculated sludge, plotted on the abscissa.

According to table I and the diagram in FIG. 4, it is apparent that for a reactor—or digester—temperature of 35° C., oxygen appears in the biogas for an oxygen concentration in the sludge of greater than or equal to 65% of X.

For a reactor temperature of 55° C., oxygen is present in the biogas for an oxygen concentration in the sludge of greater than or equal to 60% of X.

In the diagram in FIG. 4, the solid line corresponds to the reactor temperature of 35° C., while the dot-dashed line corresponds to the reactor temperature of 55° C. In this FIG. 4, the abscissa axis corresponds to the oxygen concentrations in the sludge, expressed as percentages of the oxygen saturation X in pure water. On the ordinate, the absence of oxygen in the biogas is shown by a value of 0, whereas the presence of oxygen is shown by a value of 1.

Figure 5:
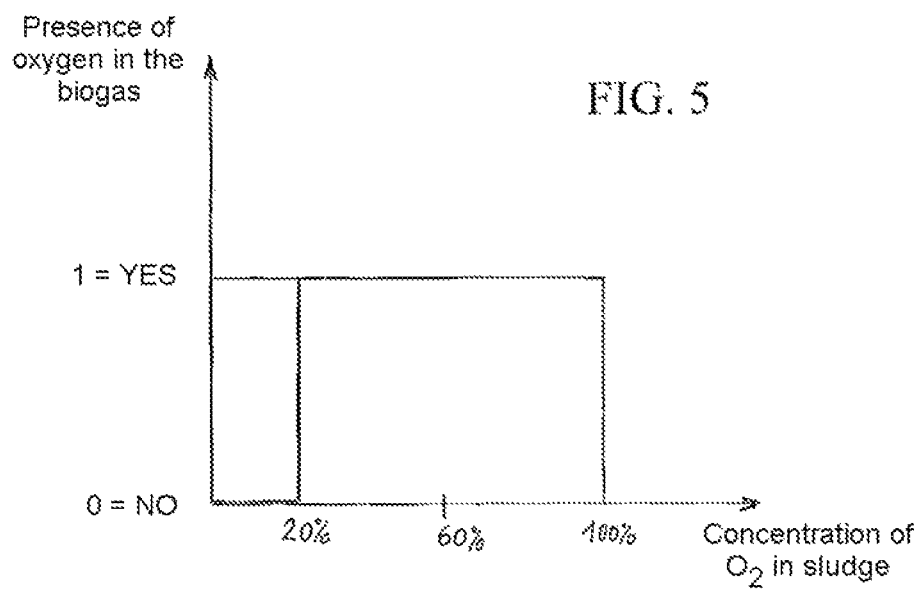
FIG. 5 is a diagram illustrating the presence of oxygen in the biogas, plotted on the ordinate, as a function of the concentration of oxygen in the recirculated sludge, plotted on the abscissa.

Table II and the diagram in FIG. 5 correspond to a contact time of less than 15 s.

TABLE II

| Concentration of oxygen in the sludge, relative to the theoretical oxygen saturation in water | Reactor temperature 35° C. | Reactor temperature 55° C. |
|---|---|---|
| 0% to 20% | Absence of oxygen in the biogas | Absence of oxygen in the biogas |
| 20% to 100% | Presence of oxygen in the biogas | Presence of oxygen in the biogas |

It is clearly evident that for oxygen concentrations in the sludge of greater than or equal to 20% of the theoretical oxygen saturation X in pure water, both at 35° C. and at 55° C., oxygen is present in the biogas. For lower concentrations, the oxygen is absent from the biogas.

Minimum Recirculation Rate

Figure 6:
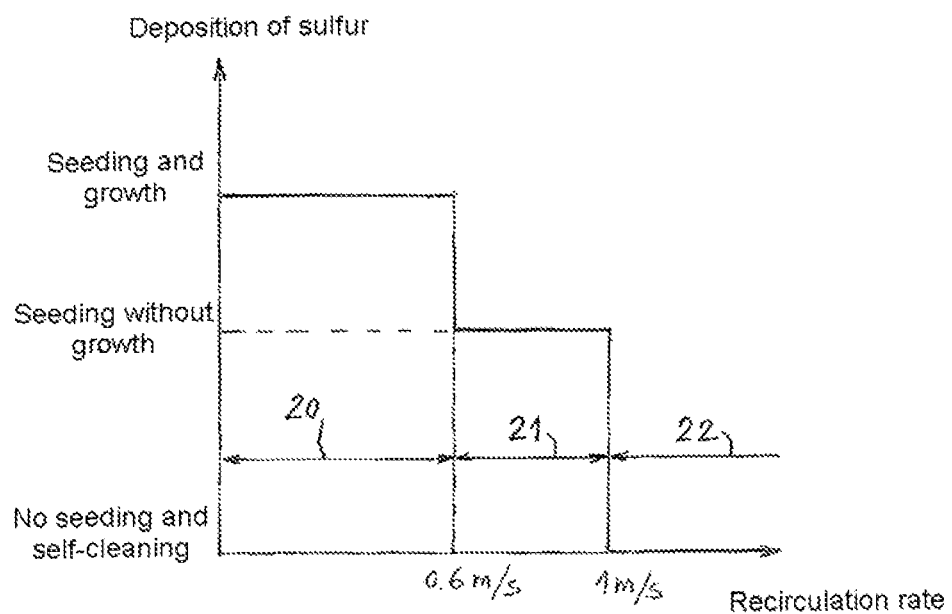
FIG. 6 is a diagram illustrating the deposition of sulfur, plotted on the ordinate, as a function of the recirculation rate in the loop, plotted on the abscissa.

The diagram in FIG. 6 summarizes the results of the tests conducted. An estimation has been made of the minimum recirculation rate to be applied in order to limit deposits of sulfur, using different diameters of recirculating lines 11. 50% oxygen saturation was selected. The tests were carried out under mesophilic (35° C.) and thermophilic (55° C.) conditions.

The feed sludge was doped with sulfates, to give a biogas of high H$_2$S loading, allowing easy visualization of the formation of sulfur in line 11. Three lines 11, with different diameters, were used in parallel, to provide a total recirculation of 2.5 m$^3$/d of sludge at three different rates at a residence time of 30 s. The flow is distributed uniformly within the three lines.

Table III hereinafter recapitulates the observations made of the formation of sulfur at different recirculation rates; since this formation is not immediate, it was necessary to carry out two to three digestion cycles for this formation to become apparent (acclimatization of the bacteria).

TABLE III

| Rate less than 0.6 m/s | Rate greater than or equal to 0.6 m/s and less than 1 m/s | Rate greater than or equal to 1 m/s |
|---|---|---|
| Formation of sulfur deposits on the line. Growth of these deposits. | Formation of sulfur particles on the wall. No growth of these deposits was observed. Erosion is continuous. | No formation of deposits on the walls, and self-cleaning of the line if a deposit has formed beforehand. Deposits on these walls are no longer observed. |

These observations were made at the two digestion temperatures of 35° C. and 55° C.

Marked accordingly was a risk zone 20 (FIG. 6) for rates of strictly less than 0.6 m/s, in which precipitation of sulfur on the walls is very great and the risks of line clogging are high. In FIG. 6, an arbitrary maximum value has been given on the ordinate, corresponding to the seeding and growth of sulfur on the wall.

For rates of between 0.6 m/s and 1 m/s, deposits are formed on the surface, but remain thin. This zone 21 (FIG. 6) is an intermediate zone, represented with an arbitrary ordinate lower than that of zone 20 in FIG. 6, corresponding to seeding on the wall but without growth. If deposits were formed at a slower rate, for example in the case of operation of digestion in degraded mode, the low rates, of less than 1 m/s, will now allow the removal of deposits once the digestion process is stabilized.

For rates of greater than 1 m/s in the recirculating line 11, there is an optimum zone 22 of operation for the desulfuration of the digestate and the biogas, without sulfur deposits on the walls.

Industrial Realization

Industrial realization is possible in accordance with the scheme in FIG. 1, in combination, where appropriate, with the variants of FIGS. 2 and 3.

The invention adapts to a digester producing biogas from one or more substrates. The hydrogen sulfide content of the biogas may be analyzed continuously by the appropriate analyzer 18 or by regular samples sent to an analytical laboratory, for example in a pouch suitable for this type of sampling.

The oxidant used in the example in question is compressed air, and the process is therefore one of microaeration rather than microoxidation. The flow rates of oxidants injected and sludges recirculated are preferably measured continuously, though this is not mandatory.

Measurement of the partial oxygen pressure in the biogas may also be provided, for example at the analyzer 18, in order to monitor any possible faulty operation; but this is not vital.

Continuous measurement of the sulfide content of the digestate and/or of the dissolved oxygen content of the digestate and/or of the redox potential of the digestate may also be used in order to prevent any faulty operation, or in order to be used for the purpose of regulating the injection of air or oxidant.

The device was installed in a plant for digestion of residual sludges from an urban purification station. The digestion plant comprises four digesters each of 15,900 m$^3$, and a 5000 m$^3$ gasometer.

Monitoring of the plant prior to the installation of microaeration shows that:
 the H$_2$S content of the biogas is 5000 ppm (parts per million),
 the average removal yield of VMs (volatile materials) is 50%, the production of biogas is 660 m³(stp)/h/digester, the production of sludges is 1.80 m³/h, the digestion temperature is 35-37° C., the sulfides to be removed came from sulfates introduced by the untreated water and the organic sulfur, in an amount in the sludges of 110 mg/l.

The height of water in the digester is 22 m (22 meters).

The recirculating line 11 is dimensioned with:

a diameter of 700 mm, a length of 40 m between the point 13 for injection of the oxidant into the loop 10, and the exit 11b from the loop.

The loop 10 is an external recirculation loop. The digestate is withdrawn from the digester bottom at a point 11a situated at a height of 2 m above the floor, in other words the base of the digester. The recirculation loop is reinjected at the point 11b, sited at the level of a digester feed trough, and hence corresponding to the liquid level in the digester.

The oxidant—in this case oxygen by compressed-air injection—was injected gradually (gradual increase in stages), so as not to disturb the biological digestion system. The oxidant is injected directly by means of a nozzle (not shown), which is sited in the recirculation line 11. The amount injected is regulated around a setpoint value linked to the amount of sulfides to be removed.

The plant was monitored for the four months following the installation of air injection.

Regular monitoring of the quality of the biogas and of the digested sludge, or one of the aforementioned regulating devices, allows adjustment to be made, if necessary, to the flow rate of air to be injected, if performance levels are changed.

Monitoring the digestion parameters is also recommended in order to counter any drift (removal yield of volatile materials, removal of COD (chemical oxygen demand), concentration of VFAs (Volatile Fatty Acids), rate of production of the biogas, etc.). It is also possible for this flow rate for injection to be regulated around a setpoint value which will be defined during commissioning of the plant.

Complete stabilization of the system is obtained after at least two digestion cycles (twice the hydraulic residence time of the substrate or effluent in the digester).

Analysis of biogas takes place twice daily and is carried out with a GA2000 portable analyzer which measures $CH_4$, $CO_2$, $HO_2$, $H_2S$, and CO (carbon monoxide).

Analysis of sulfides in the digestate, and in the feed to the digester, is carried out weekly by spectro-photometry.

The material balance evaluates the amount of sulfides present in the biogas (equivalent to $H_2S$), to which the sulfides found in the digestate are added. The efficiency of the method is measured on the reduction in level of sulfides relative to the level at the entry of the digester.

The results of this implementation example were obtained with continuous injection of air into the recirculation loop of the digester. For reasons of practicality, however, a cyclical injection of air may be used. However, attention must be paid to injecting air for at least 10 minutes each hour, in order to maintain the microbiology of the reaction. The air flow rate was increased in stages.

The results obtained are given in table IV below.

TABLE IV

| Duration of experiment | Amount of air injected (%) relative to the design of the loop | Reduction in level of sulfides (%) $1 - \dfrac{\text{Sulfides eg. biogas} + \text{sulfides eg. digestate}}{\text{Sulfides at entry of digester}}$ in % |
|---|---|---|
| T0 (prior to installation of the equipment) | 0 | 0% |
| T0 to T0 + 7d | 10% | 2% |
| T0 + 7d to T0 + 14d | 20% | 5% |
| T0 + 14d to T0 + 21d | 30% | 10% |
| T0 + 21d to T0 + 28d | 40% | 20% |
| T0 + 28d to T0 + 35d | 50% | 35% |
| T0 + 35d to T0 + 42d | 60% | 45% |
| T0 + 42d to T0 + 49d | 70% | 60% |
| T0 + 49d to T0 + 56d | 80% | 70% |
| T0 + 56d to T0 + 63d | 90% | 75% |
| T0 + 63d to T0 + 70d | 100% | 83% |
| T0 + 100d | 100% | 80% |

These results were obtained with the digesters being fed throughout the period of the tests. The production of biogas remained similar, to within at +/−10%, and the digestion yield (Van Klick type) is also preserved.

Also observed was a decrease in the concentration of $H_2S$ at the entry to the deodorization facility of the wastewater station in the course of the tests. However, since deodorization affects all of the buildings in the purification station, it is not possible to demonstrate the sole impact of microaeration on the amount of sulfides in the air coming from the ventilation network of the whole of the station.

The efficacy of the treatment could have been improved to values of close to 100% by increasing the flow rate of oxidant, but for the purposes of this example an efficacy of 80% was sufficient for reducing the level of sulfides.

INDUSTRIAL APPLICATIONS

Any anaerobic digester or methanizer or fermenter operating by the dry and/or wet route and capable of treating one or more effluents and/or one or more substrates, irrespective of the operating temperature of the method, can be the subject of the implementation of the invention.

The method can be installed by formation of a sludge recirculation loop through manholes in the digestion or methanization or fermentation apparatus, or at sample withdrawal points situated on the dome (or roof) or in the periphery of the digester.

The agitation of the digester may be mechanical agitation of screw type, as illustrated in FIG. 7, or any other vertical and/or horizontal mechanical agitation system, or agitation with biogas, with an agitating pipe in accordance with FIG. 8 or a bubble canister in accordance with FIG. 9 or other such system, or a hydraulic system, with recirculation, or other such system.

The invention relates to methanization plants which produce a biogas that can contain up to 20,000 ppm of $H_2S$ and more particularly from 0 to 10,000 ppm, and more particularly still from 0 to 5000 ppm.

The purified biogas has a hydrogen sulfide content of not more than 50 ppm, depending on the operating conditions.

The invention promotes the dissolution of oxygen in the digestate and prevents the appearance of stalactites under the dome of the digester, in the gas space.

The invention adapts to any digester which produces biogas from one or more substrates. The hydrogen sulfide content of the biogas may be analyzed continuously by an appropriate analyzer or by regular samples sent to an analytical laboratory (by special pouch, for example).

When the oxidant used is compressed air, microaeration is the term used. The rates of oxidant injected and of biogas are preferably measured continuously, but this is not mandatory. Measurement of the oxygen partial pressure in the biogas may also be provided, in order to monitor any faulty operation.

Continuous measurement of the sulfide content in the digestate and/or of the dissolved oxygen content in the digestate and/or of the redox potential of the digestate may also be used in order to prevent any faulty operation or for purposes of regulating the injection of air or oxidant.

The invention claimed is:

1. A method for desulfuration of a digestate and a biogas in a digester for urban and/or agricultural and/or industrial effluents, by wet and/or dry route, the digester comprising a chamber which is closed at the top and in which anaerobic digestion of a mass of products to be treated takes place, forming the digestate, with a gas space above the digestate, from which the biogas is withdrawn, the digester comprising at least one external digestate recirculation loop, wherein:
   a digestate withdrawal point is situated in the lower part of the digester, and the digestate is reinjected at a point at a liquid level higher than the withdrawal point,
   at least one point of the digestate recirculation loop, a gaseous or liquid oxidant is injected, the injection conditions being as follows:
   a circulation rate of the digestate in the loop is sufficient to prevent the deposition of sulfur on the walls of the lines in the recirculation loop,
   a contact time between the injected oxidant and the recirculated digestate, from the point of injection of the oxidant to a point of reintroduction of the digestate in the chamber, is sufficient for all of the oxidant to be dissolved in a liquid phase of the digestate,
   the amount of oxygen in the oxidant injected into the digestate is low enough to prevent a presence of oxygen in the biogas but high enough to remove hydrogen sulfide from the biogas,
   a sulfur produced remaining in the form of particles which are dispersed in the digestate and being removed together with the digestate.

2. The method as claimed in claim 1, wherein the amount of air or oxygen injected into the recirculation loop corresponds to the amount that would produce an equivalent oxygen concentration of less than or equal to 0.65 X, where X is the saturation concentration of oxygen in pure water, estimated at the temperature and pressure of the recirculation loop.

3. The method as claimed in claim 1, wherein the amount of air or oxygen injected into the recirculation loop corresponds to the amount that would produce an equivalent oxygen concentration of greater than or equal to 0.20 X, where X is the saturation concentration of oxygen in pure water, estimated at the temperature and pressure of the recirculation loop.

4. The method as claimed in claim 2, wherein the amount of air or oxygen injected into the recirculation loop corresponds to the amount that would produce an equivalent oxygen concentration of between 0.60 X and 0.20 X, where X is the saturation concentration of oxygen in pure water, estimated at the temperature and pressure of the recirculation loop.

5. The method as claimed in claim 1, wherein the contact time between the injected oxidant and the digestate, from the point of injection to the point of reintroduction into the chamber, is at least 15 seconds.

6. The method as claimed in claim 1, wherein the circulation rate of the digestate in the loop is at least 0.6 m/s.

7. The method as claimed in claim 1, wherein the oxidant injected is gaseous and composed of air or oxygen.

8. A plant for producing biogas, comprising a digester for urban and/or agricultural and/or industrial effluents, by wet and/or dry route, the digester comprising a chamber which is closed at the top and in which anaerobic digestion of a mass of products to be treated takes place, forming a digestate, with a gas space above the digestate, from which the biogas is withdrawn, and at least one external digestate recirculation loop between a point of withdrawal from the chamber and a reintroduction point, wherein:
   the withdrawal point of the digestate is situated in the lower part of the digester, and the digestate is reinjected at a point at a liquid level higher than the withdrawal point,
   said plant comprises, at least one point in the recirculation loop, a device (D) for injecting a gaseous or liquid oxidant,
   said plant includes a pump which circulates the digestate within the loop, the diameter of the piping of the loop and the capacity of the pump being selected such that the circulation rate of the digestate in the loop is sufficient to prevent deposition of sulfur on the walls of the lines in the recirculation loop,
   the length of piping in the loop between the injection point and the reintroduction point in the chamber is sufficient for all of the oxidant to pass into a liquid phase of the digestate before return to the chamber,
   and the amount of oxygen in the oxidant injected in the recirculation loop is low enough to prevent the presence of oxygen in the biogas and high enough to remove hydrogen sulfide from the biogas.

9. The plant as claimed in claim 8, wherein the recirculation loop includes a contact basin, more particularly with agitating means, to promote transfer of the oxidant into a recirculated phase.

10. The plant as claimed in claim 8, wherein the digestate withdrawal point for the recirculation loop is situated in the lower part of the digester, and the digestate reintroduction point is situated at a liquid level higher than the withdrawal point, so as to limit a degassing of the oxidant.

11. The plant as claimed in claim 8, wherein the recirculation loop includes at least one heat exchanger for reheating the digestate and maintaining the digester at constant temperature.

12. The plant as claimed in claim 11, wherein the heat exchanger is a double-wall exchanger around a portion of the recirculation loop.

13. The method as claimed in claim 6, wherein the circulation rate of the digestate in the loop is at least 1 m/s.

* * * * *